(12) United States Patent
Parsons et al.

(10) Patent No.: US 8,486,081 B2
(45) Date of Patent: Jul. 16, 2013

(54) IMPLANT INSERTION DEVICE AND METHOD

(75) Inventors: Matthew Parsons, Dartmouth, MA (US); Douglas D. Raymond, Randolph, MA (US); Thomas E. Martin, Riverside, RI (US)

(73) Assignee: DePuy Synthes Products, LLC, Raynham, MA (US)

( * ) Notice: Subject to any disclaimer, the term of this patent is extended or adjusted under 35 U.S.C. 154(b) by 615 days.

(21) Appl. No.: 11/880,561

(22) Filed: Jul. 23, 2007

(65) Prior Publication Data

US 2009/0030422 A1 Jan. 29, 2009

(51) Int. Cl.
*A61B 17/56* (2006.01)

(52) U.S. Cl.
USPC .......................................................... 606/99

(58) Field of Classification Search
USPC .................... 606/86 A, 86 R, 90, 96, 99, 105; 623/17.11–17.16
See application file for complete search history.

(56) References Cited

U.S. PATENT DOCUMENTS

| | | | |
|---|---|---|---|
| 4,898,161 A | 2/1990 | Grundei | |
| 4,997,432 A | 3/1991 | Keller | |
| 5,431,658 A | 7/1995 | Moskovich | |
| 5,720,751 A | 2/1998 | Jackson | |
| 6,017,342 A | 1/2000 | Rinner | |
| 6,063,088 A | 5/2000 | Winslow | |
| 6,066,174 A | 5/2000 | Farris | |
| 6,228,022 B1 * | 5/2001 | Friesem et al. | 600/204 |
| 6,261,296 B1 | 7/2001 | Aebi et al. | |
| 6,319,257 B1 | 11/2001 | Carignan et al. | |
| 6,440,142 B1 | 8/2002 | Ralph et al. | |
| 6,478,800 B1 | 11/2002 | Fraser et al. | |
| 6,551,316 B1 | 4/2003 | Rinner et al. | |
| 6,565,570 B2 | 5/2003 | Sterett et al. | |
| 6,569,168 B2 | 5/2003 | Lin | |
| 6,652,533 B2 * | 11/2003 | O'Neil | 606/100 |
| 6,663,638 B2 | 12/2003 | Ralph et al. | |
| 6,712,825 B2 | 3/2004 | Aebi et al. | |
| 6,716,218 B2 | 4/2004 | Holmes et al. | |

(Continued)

FOREIGN PATENT DOCUMENTS

| | | |
|---|---|---|
| EP | 1 295 578 A2 | 3/2003 |
| EP | 1323 396 A2 | 7/2003 |
| EP | 1459712 A2 | 9/2004 |
| WO | WO 2004089224 A2 | 10/2004 |

OTHER PUBLICATIONS

Johnson & Johnson: DepuySpine, *Surgical Technique*, Charité™ Artificial Disc Centerline™ TDR (19 pages).

(Continued)

*Primary Examiner* — Kevin T Truong
*Assistant Examiner* — Christopher Beccia
(74) *Attorney, Agent, or Firm* — Maginot, Moore & Beck LLP

(57) ABSTRACT

A method and system for insertion of an implant is disclosed. One embodiment of a system for use in implanting a spinal prosthesis incorporating principles of the invention includes an insertion assembly housing with a channel extending from a distal end portion to a proximal end portion, a gripper having a prosthesis coupling portion for coupling with a spinal prosthesis and an end portion, and a coupler member having a gripper coupling portion rotatably positioned within the channel and configured to couple with the end portion of the gripper within the channel.

19 Claims, 13 Drawing Sheets

U.S. PATENT DOCUMENTS

| | | | |
|---|---|---|---|
| 6,746,454 B2 | 6/2004 | Winterbottom et al. | |
| 6,755,841 B2 * | 6/2004 | Fraser et al. | 606/99 |
| 6,814,737 B2 | 11/2004 | Cauthen | |
| 6,896,676 B2 | 5/2005 | Zubok et al. | |
| 6,896,680 B2 | 5/2005 | Michelson | |
| 6,986,772 B2 | 1/2006 | Michelson | |
| 7,008,432 B2 | 3/2006 | Schläpfer et al. | |
| 7,278,995 B2 * | 10/2007 | Nichols et al. | 606/272 |
| 7,320,689 B2 * | 1/2008 | Keller | 606/99 |
| 7,708,760 B2 * | 5/2010 | Parsons | 606/247 |
| 2002/0072752 A1 | 6/2002 | Zucherman et al. | |
| 2002/0128659 A1 | 9/2002 | Michelson | |
| 2003/0130667 A1 | 7/2003 | Lin | |
| 2003/0149438 A1 | 8/2003 | Nichols et al. | |
| 2003/0225416 A1 | 12/2003 | Bonvallet et al. | |
| 2003/0229358 A1 | 12/2003 | Errico et al. | |
| 2003/0233145 A1 | 12/2003 | Landry et al. | |
| 2004/0002758 A1 | 1/2004 | Landry et al. | |
| 2004/0039397 A1 | 2/2004 | Weber et al. | |
| 2004/0102790 A1 | 5/2004 | Ralph et al. | |
| 2004/0106927 A1 | 6/2004 | Ruffner et al. | |
| 2004/0167534 A1 | 8/2004 | Errico et al. | |
| 2004/0167535 A1 | 8/2004 | Errico et al. | |
| 2004/0167536 A1 | 8/2004 | Errico et al. | |
| 2004/0167537 A1 | 8/2004 | Errico et al. | |
| 2004/0176773 A1 | 9/2004 | Zubok et al. | |
| 2004/0181233 A1 | 9/2004 | Michelson | |
| 2004/0220582 A1 | 11/2004 | Keller | |
| 2004/0225295 A1 * | 11/2004 | Zubok et al. | 606/90 |
| 2004/0243240 A1 | 12/2004 | Beaurain et al. | |
| 2005/0015094 A1 * | 1/2005 | Keller | 606/99 |
| 2005/0027300 A1 | 2/2005 | Hawkins et al. | |
| 2005/0043741 A1 | 2/2005 | Michelson | |
| 2005/0075644 A1 | 4/2005 | DiPoto et al. | |
| 2005/0113842 A1 | 5/2005 | Bertagnoli et al. | |
| 2005/0119665 A1 | 6/2005 | Keller | |
| 2005/0143747 A1 | 6/2005 | Zubok et al. | |
| 2005/0143749 A1 | 6/2005 | Zalenski et al. | |
| 2005/0159756 A1 | 7/2005 | Ray | |
| 2005/0165408 A1 * | 7/2005 | Puno et al. | 606/99 |
| 2005/0216085 A1 | 9/2005 | Michelson | |
| 2005/0228400 A1 | 10/2005 | Chao et al. | |
| 2006/0004376 A1 | 1/2006 | Shipp et al. | |
| 2006/0004377 A1 | 1/2006 | Keller | |
| 2006/0025777 A1 | 2/2006 | Weber | |
| 2006/0030860 A1 | 2/2006 | Peterman | |
| 2006/0084986 A1 | 4/2006 | Grinberg et al. | |
| 2006/0089656 A1 | 4/2006 | Allard et al. | |
| 2006/0095043 A1 * | 5/2006 | Martz et al. | 606/90 |
| 2006/0167461 A1 | 7/2006 | Hawkins et al. | |
| 2006/0195097 A1 * | 8/2006 | Evans et al. | 606/61 |
| 2006/0264968 A1 | 11/2006 | Frey et al. | |
| 2007/0093850 A1 * | 4/2007 | Harris et al. | 606/99 |
| 2007/0100453 A1 | 5/2007 | Parsons et al. | |
| 2008/0275455 A1 * | 11/2008 | Berry et al. | 606/99 |
| 2009/0030422 A1 * | 1/2009 | Parsons et al. | 606/99 |

OTHER PUBLICATIONS

European Search Report referencing application No. PCT/US2008/008757 dated Apr. 2, 2012 (8 pages).

* cited by examiner

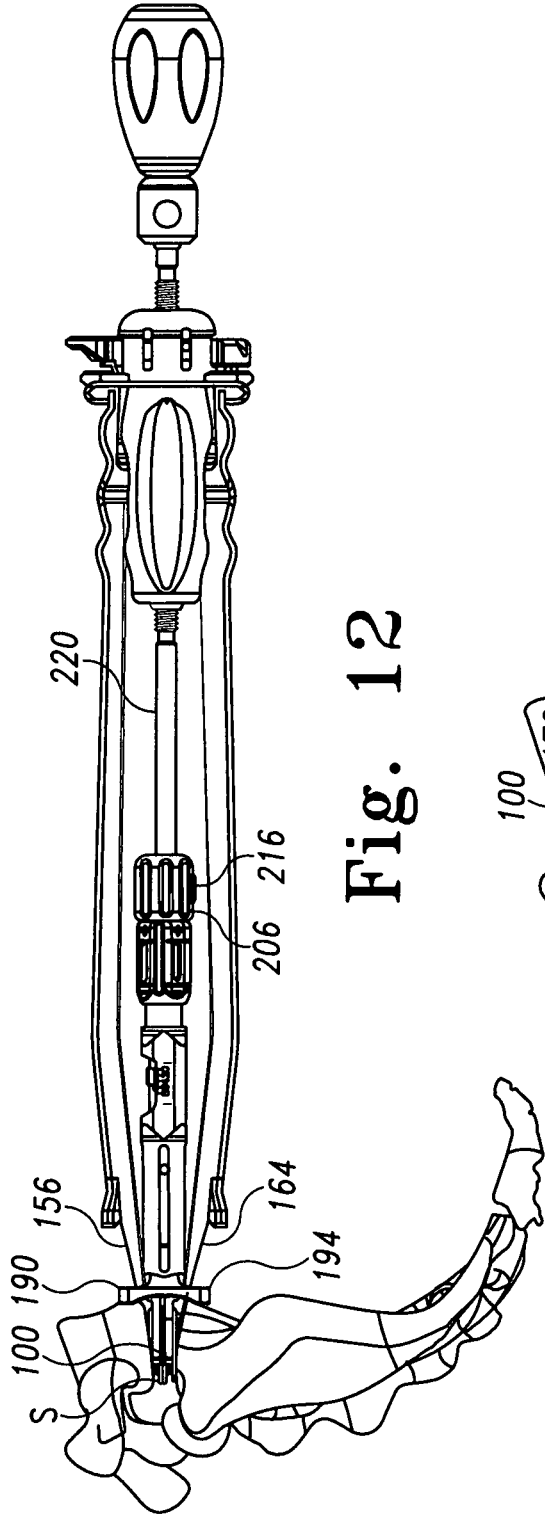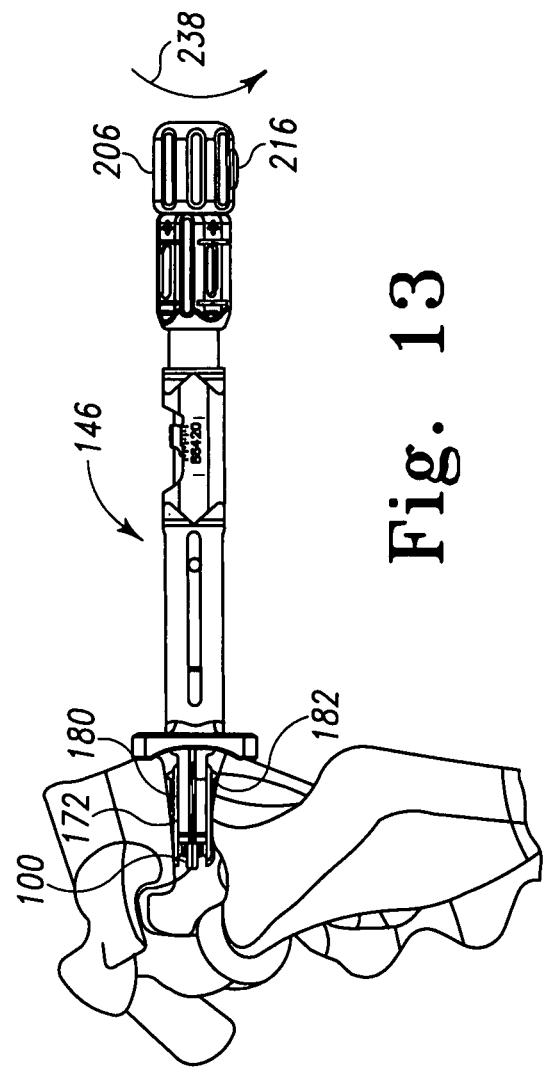

IMPLANT INSERTION DEVICE AND METHOD

FIELD OF THE INVENTION

This invention relates to surgical methods and devices and, more particularly, to methods and devices used to facilitate insertion of implants.

BACKGROUND

The spine is made of bony structures called vertebral bodies that are separated by soft tissue structures called intervertebral discs. The intervertebral disc is commonly referred to as a spinal disc. The spinal disc primarily serves as a mechanical cushion between the vertebral bones, permitting controlled motions between vertebral segments of the axial skeleton. The disc acts as a synchondral joint and allows some amount of flexion, extension, lateral bending, and axial rotation.

The normal disc is a mixed avascular structure including two vertebral end plates, annulus fibrosis and nucleus pulposus. The end plates are composed of thin cartilage overlying a layer of hard, cortical bone that attaches to the spongy cancellous bone of the adjacent vertebral body.

The discs are subjected to a variety of loads as the posture of an individual changes. Even when the effects of gravity are removed, however, the soft tissue connected to the spine generates a compressive force along the spine. Thus, even when the human body is supine, the compressive load on the lumbar disc is on the order of 300 Newtons (N).

A spinal disc may be displaced or damaged due to trauma or a disease process. A disc herniation occurs when the annulus fibers are weakened or torn and the inner material of the nucleus becomes permanently bulged, distended, or extruded out of its normal, internal annular confines. The mass of a herniated or "slipped" nucleus tissue can compress a spinal nerve, resulting in leg pain, loss of muscle strength and control or even paralysis. Alternatively, with discal degeneration, the nucleus loses its water binding ability and dehydrates with subsequent loss in disc height. Consequently, the volume of the nucleus decreases, causing the annulus to buckle in areas where the laminated plies are loosely bonded. As these overlapping plies of the annulus buckle and separate, either circumferential or radial annular tears may occur, potentially resulting in persistent and disabling back pain. Adjacent, ancillary facet joints will also be forced into an overriding position, which may cause additional back pain.

When the discs wear out or are otherwise injured, a condition known as degenerative disc disease results. With this condition, discs do not function normally and may cause pain and limit activity. Recently, efforts have been directed to replacing intervertebral discs which display degenerative disc disease. In one such procedure, the damaged intervertebral disc is replaced by a prosthetic disc.

One well known intervertebral prosthetic disc is produced by DePuy Spine, Inc. of Raynaham, Mass. and is sold under the trademark CHARITÉ®. This disc prosthesis includes two metal endplates and a center polyethylene core. The center core includes a superior spherical bearing surface and an inferior spherical bearing surface. The superior endplate includes a concave surface that fits upon and is congruent with the superior bearing surface of the core. The inferior endplate includes a concave surface that fits under and is congruent with the inferior bearing surface of the core.

During a CHARITÉ® artificial disc replacement procedure, the damaged disc is typically removed via an anterior surgical approach and the end surfaces of the exposed vertebrae are cleared of debris. The vertebrae are spread apart and the metal endplates are positioned on the respective vertebra and tapped into place. The polyethylene core is then inserted between the endplates and the vertebrae are returned to their normal position. The pressure of the spinal column further seats the endplates into the vertebral bones and secures the core in place.

While the sequential implantation of components is effective, the amount of time required to position three separate components as opposed to implanting a single unit increases the duration of the procedure. Additionally, the increased number of steps increases the risk of the procedure.

In response to the foregoing limitations, some instrumentation has been developed wherein a distraction instrument may also serve as an installation instrument. In particular, in addition to being configured to spread apart the two vertebrae, the instrument is also configured to slide the assembled artificial disc into place while the vertebrae remain separated. A central ramp is provided on the instrument to facilitate sliding of the implant between the vertebrae. Once the artificial disc is positioned, the installation instrument is decoupled from the artificial disc and removed.

Such instruments are very effective. Nonetheless, they do have various limitations. For example, because of the various functions performed with the instrument, the instruments are complicated in construction, resulting in increased costs. Additionally, as a particular instrument becomes more complicated, the potential for a mechanical failure increases. A further limitation is that the artificial disc is retained in such instruments using spring force which can be unreliable.

Accordingly, it would be advantageous to provide a tool for implanting an artificial disc or other spinal implant which does not rely upon a spring to maintain a secure hold upon the artificial disc or other spinal implant. It would also be advantageous if the tool could be used in combination with a distraction tool. It would be further advantageous if such features could be provided while allowing an artificial disc or other spinal implant to be implanted as a unit.

SUMMARY

A method and system for insertion of an implant is disclosed. One embodiment of a system for use in implanting a spinal prosthesis incorporating principles of the invention includes an insertion assembly housing with a channel extending from a distal end portion to a proximal end portion, a gripper having a prosthesis coupling portion for coupling with a spinal prosthesis and an end portion, and a coupler member having a gripper coupling portion rotatably positioned within the channel and configured to couple with the end portion of the gripper within the channel.

One method incorporating principles of the invention includes identifying a vertebral implant, coupling a gripper member with the vertebral implant, rotating a coupler member within a housing to generate an axial force, translating the axial force to a compressive force on the gripper member, positioning the coupled vertebral implant, removing the compressive force from the gripper member and decoupling the gripper member from the vertebral implant after the vertebral implant has been positioned.

Another system for use in implanting a spinal implant includes an insertion assembly housing having an axis, a gripper with a spinal implant coupling portion configured to couple with a spinal implant and a coupling member configured to apply force to the gripper along the axis of the insertion assembly housing by rotation of the coupling member within the insertion assembly housing.

The above-described features and advantages, as well as others, will become more readily apparent to those of ordinary skill in the art by reference to the following detailed description and accompanying drawings.

BRIEF DESCRIPTION OF THE DRAWINGS

The present invention may take form in various system and method components and arrangement of system and method components. The drawings are only for purposes of illustrating exemplary embodiments and are not to be construed as limiting the invention.

FIG. 12 shows a side plan view of the system of FIG. 3 after continued rotation of the knob of the distraction instrument has forced the fingers of the distraction instrument out of the space in the spine while the disc prosthesis remains in the space in accordance with principles of the invention;

FIG. 13 shows a side plan view of the system of FIG. 3 after the distraction instrument has been removed and while the gripper and the prosthesis insertion assembly are still coupled;

DETAILED DESCRIPTION

Figure 1:
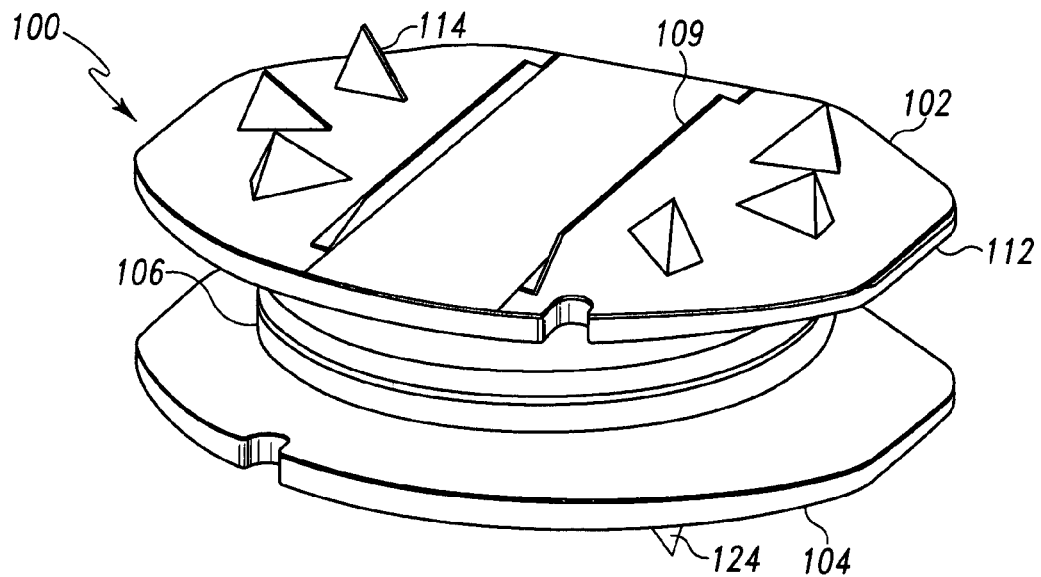
FIG. 1 shows a superior perspective view of a spinal implant in the form of an intervertebral disc prosthesis including a superior plate and a inferior plate separated by a core.
Figure 2:
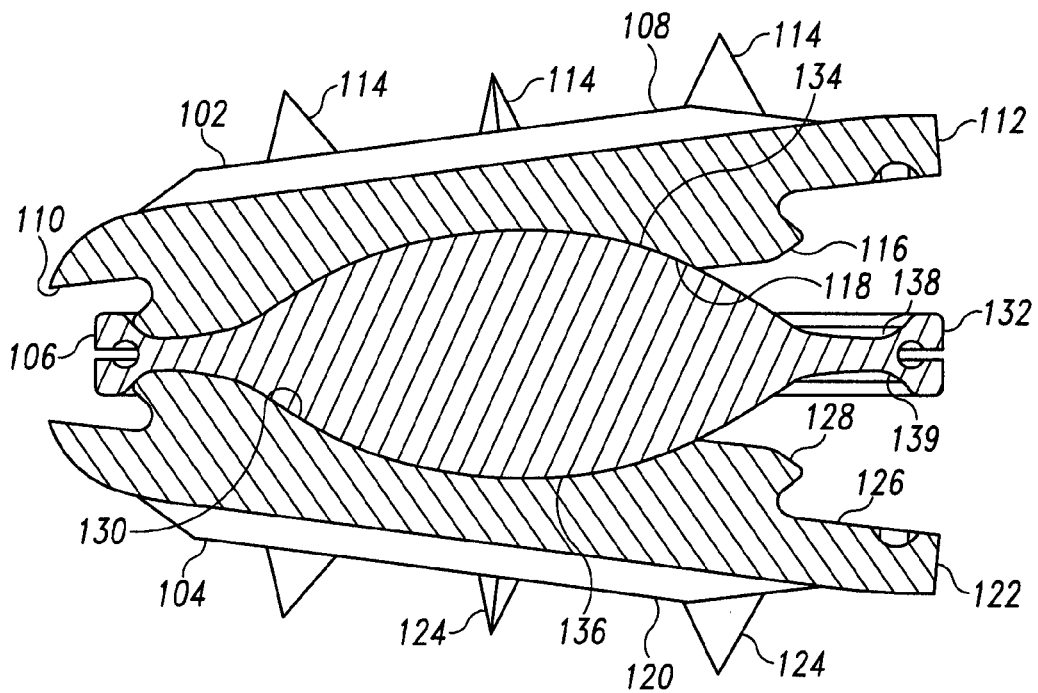
FIG. 2 shows a side cross-sectional view of the intervertebral disc prosthesis of FIG. 1 with the superior plate rotated to display flexion.

With reference to FIGS. 1-2, a spinal implant which in this embodiment is an intervertebral disc prosthesis 100 includes a superior plate 102, an inferior plate 104, and a core 106. The core 106 is sandwiched between the superior plate 102 and the inferior plate 104. The superior plate 102 and the inferior plate 104 ride upon the core 106 and are operable to rotate relative to the core 106.

In one embodiment, the superior plate 102 is formed of metal. In particular, the superior plate 102 may be formed using a medical grade cobalt chromium alloy. The superior plate 102 includes an upper surface 108 and a lower surface 110. An outer perimeter edge 112 defines the "footprint" of the superior plate 102 when the disc prosthesis is implanted.

The upper surface 108 of the superior plate 102 is designed for engagement with a vertebral surface of a patient. To this end, the upper surface 108 of the superior plate 102 may be slightly convex for close engagement with the slightly concave vertebral surface of the patient. Additionally, teeth 114 are included on the upper surface 108 of the superior plate 102. The teeth 114 are designed to penetrate into the vertebral surface, helping to secure the superior plate 102 to the vertebral surface. A groove 109 extends across the upper surface 108.

The lower surface 110 of the superior plate 102 is generally flat near the outer edge 112. As shown more clearly in FIG. 2, a collar portion 116 protrudes from the lower surface 110 and defines an inner concave surface 118 at the center of the collar portion 116.

The inferior plate 104 is a mirror image of the superior plate 102 and is also made of a medical grade cobalt chromium alloy. The inferior plate 104 includes a slightly convex lower surface 120 and an outer perimeter edge 122. A plurality of teeth 124 extend from the lower surface 120. The teeth 124 are designed to help secure the inferior plate 104 to a vertebral surface. The lower surface 120 also includes a groove (not shown). The upper surface 126 of the inferior plate 104 includes a collar portion 128 with an inner concave surface 130.

The core 106 is arranged within an interior space of the prosthesis 100 between the lower surface 110 of the superior plate 102 and the upper surface 126 of the inferior plate 104. In one embodiment, the prosthesis core 106 is made from a plastic material having a high resistance to wear, such as ultra high molecular weight polyethylene (UHMWPE), which allows the endplates 102 and 104 to slide easily on the core 106.

The prosthesis core 106 is generally disc shaped with an outer radial flange 132, an upper spherical surface 134, and a lower spherical surface 136. The upper spherical surface 134 and the lower spherical surface 136 act as bearing surfaces/articulating surfaces that slidingly engage the bearing/articulating surfaces of the endplates 102 and 104. Namely, the inner concave surface 118 and the inner concave surface 130, respectively. As shown in FIG. 2, a first groove 138 is formed between the flange 132 and the collar portion 116 of the superior plate 102. A second groove 139 is formed between the flange 132 and the collar portion 128 of the inferior plate 104.

When the prosthesis 100 is assembled, the concave surface 118 of the superior plate 102 and the upper spherical surface 134 of the core 106 slidingly engage one another and form articular surfaces. Likewise, the concave surface 130 of the inferior plate 104 and the lower spherical surface 136 of the core 106 slidingly engage one another and form articular surfaces.

Figure 3:
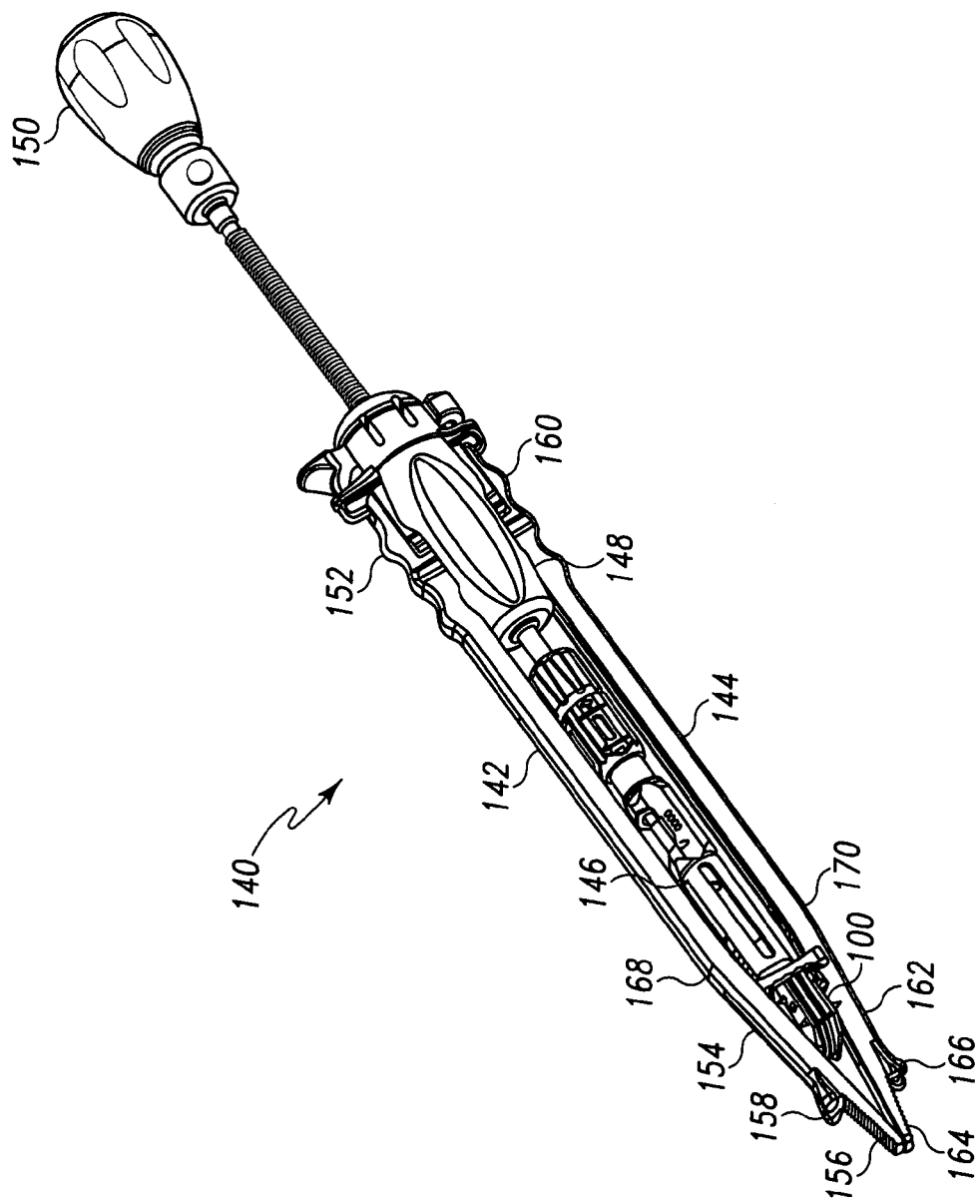
FIG. 3 shows a perspective view of the disc prosthesis of FIG. 1 held by a system including a distraction instrument and a prosthesis insertion assembly incorporating features of the invention.

A tool that may be used to position the prosthesis 100 within a patient is shown in FIG. 3. The intervertebral distraction instrument 140 includes a first vertebra engaging member 142, a second vertebra engaging member 144, and a prosthesis insertion assembly 146. A base 148, which in this embodiment further functions as a handle, is located between the first vertebra engaging member 142 and the second vertebra engaging member 144. A knob 150 is located rearward of the engaging members 142 and 144.

In the embodiment of FIG. 3, the first vertebra engaging member 142 is provided as an upper elongated distraction arm. The vertebra engaging member 142 includes a proximal end portion 152 and a distal end portion 154. A finger 156 extends from the vertebra engaging member 142 at the distal end portion 154. The finger 156 is a relatively thin tab with a vertebra engaging member 158 on the upper portion of the tab.

The second vertebra engaging member 144 is provided as a lower elongated distraction arm, and is generally symmetric to the upper vertebra engaging member 142. Accordingly, the vertebra engaging member 144 includes a proximal end portion 160, a distal end portion 162, and a finger 164. The finger 164 includes a vertebra engaging member 166.

The upper vertebra engaging member 142 and the lower vertebra engaging member 144 are configured such that the finger 156 and the finger 164 converge. In the embodiment of FIG. 3, this is accomplished by the provision of a bend 168 in the vertebra engaging member 142 and a bend 170 in the vertebra engaging member 144. The bends 168 and 170 are located between the respective proximal end portion 152 or 160 and finger 156 or 164 such that the fingers 156 and 164 converge.

The prosthesis insertion assembly 146 is positioned between the vertebra engaging member 142 and the vertebra engaging member 144. The prosthesis insertion assembly 146 is shown with a gripper 172 in FIG. 4 and includes an outer prosthesis insertion assembly housing 174 positioned outwardly of an inner sleeve 175. The gripper 172 includes a stem 176 with a gap 178 that extends along a portion of the stem 176. A pair of arms 180 and 182 are connected to the stem 176 through a neck portion 184. A blind threaded bore 186 is located within the stem 176 at the end of the gripper 172 opposite to the arms 180 and 182.

The outer prosthesis insertion assembly housing 174 includes guide members 188, 190, 192 and 194 (see also FIG. 5) while an inner channel 196 is defined by the inner sleeve 175. A throat 198 is located within the inner channel 196 (see, e.g., FIG. 7) proximate to one end portion 200 of the prosthesis insertion assembly housing 174 while the other end portion 202 of the housing 174 is externally threaded.

Figure 6:
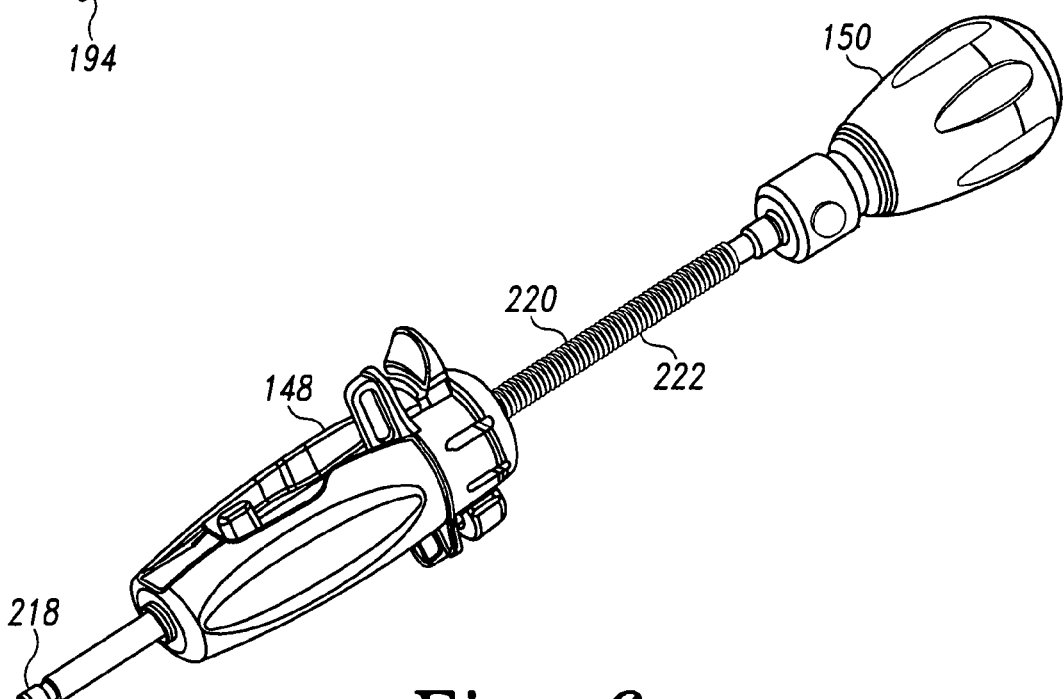
FIG. 6 shows a perspective view of the base and knob portion of the system of FIG. 3 decoupled from the prosthesis insertion assembly and with the vertebra engaging members removed.

The prosthesis insertion assembly 146 further includes a depth control member 204 and a coupling member 206. The depth control member 204 is rotatably engaged with the inner sleeve 175 and includes an internally threaded bore 208 which extends completely through the depth control member 204. The coupling member 206 includes a stem 210 with a threaded portion 212. The coupling member 206 is rotatably connected to the depth control member 204 and further includes an internal bore 214 and a release mechanism 216 which extends into the internal bore 214. The internal bore 214 is configured to receive a coupling portion 218 of a shaft 220 shown in FIG. 6. The shaft 220 extends through the base 148 and is connected to the knob 150. A threaded portion 222 of the shaft 220 threadingly engages the base 148.

Operation of the insertion distraction instrument 140 may begin with the upper and lower vertebra engaging members disconnected and the prosthesis insertion assembly 146 decoupled from the shaft 220. In such a procedure, the desired insertion depth is set by rotation of the depth control member 204. The desired depth, which may be shown on an indicator 223 (see FIG. 8), may be established with the depth control member 204 at any time.

As the depth control member 204 is rotated, the threads of the internally threaded bore 208 engage the threads of the threaded end portion 202 of the outer prosthesis insertion assembly housing 174 causing relative movement between the outer prosthesis insertion assembly housing 174 and the inner sleeve 175 to which the depth control member 204 is rotatably engaged. Accordingly, the axial position of the guides 188, 190, 192 and 194 with respect to the throat 198 within the inner channel 196 may be adjusted. The insertion depth thus identifies the desired positioning of a disc prosthesis within a spinal column along the longitudinal axis of the instrument 140 when the disc prosthesis is inserted as discussed below.

Figure 7:
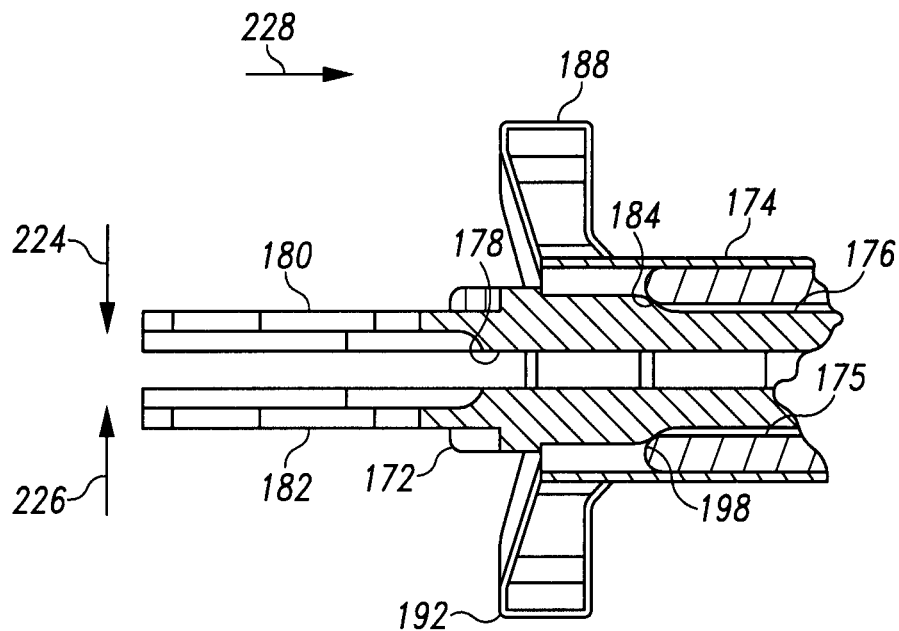
FIG. 7 is a partial cross-sectional view of the prosthesis insertion assembly of FIG. 3 with a gripper partially inserted into the housing of the prosthesis insertion assembly such that the neck portion of the gripper abuts the throat portion of the prosthesis insertion assembly.

Continuing with the present example, once the desired depth setting has been established, the stem 176 of the gripper 172 is inserted into the inner channel 196 through the end portion 200. The stem 176 is sized to pass through the throat 198. The neck portion 184, however, is tapered from a diameter somewhat smaller than the diameter of the throat 198 to a diameter somewhat larger than the throat 198 as shown in FIG. 7. Accordingly, once the neck portion 184 contacts the throat 198, further axial movement of the stem 176 into the inner channel 196 is inhibited.

The disc prosthesis 100 is then coupled with the gripper 172. In this embodiment, the gripper 172 is sized to provide a friction fit for a prosthesis 100 of a specific size. Specifically, the arms 180 and 182 are sized and shaped to frictionally engage the prosthesis 100 by insertion of the arms 180 and 182 into the slot 109 and the slot (not shown) on the lower surface 120 of the inferior plate 104. Accordingly, a kit may include a number of different grippers for use with differently sized and/or configured disc prostheses. In this embodiment the prosthesis 100 is a modular disc prosthesis and the arms 180 and 182 are configured to hold the assembled modular disc prosthesis together as a unit.

Figure 8:
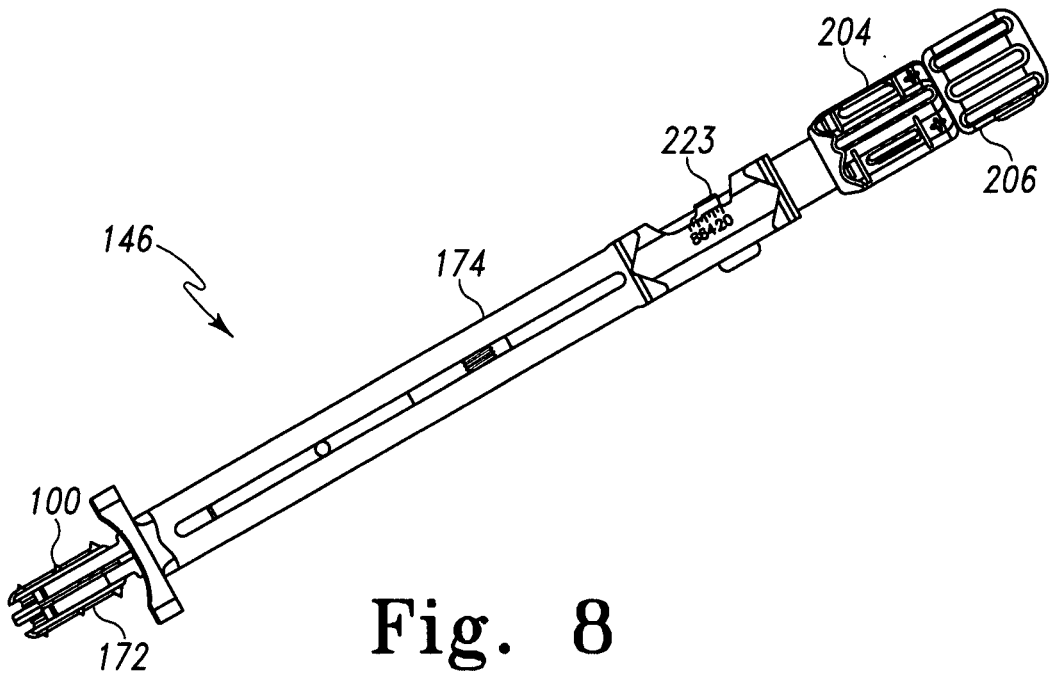
FIG. 8 shows a side plan view of the prosthesis insertion assembly of FIG. 3 with a disc prosthesis coupled with a gripper which is partially inserted into the prosthesis insertion assembly and with the coupling member removed.

If desired, the foregoing steps may be performed in a different order if desired. For example, the gripper 172 and the disc prosthesis 100 may be coupled prior to insertion of the gripper 172 within the prosthesis insertion assembly housing 174. The gripper 172 may then be positioned within the housing 174 as shown in FIG. 8.

Figure 4:
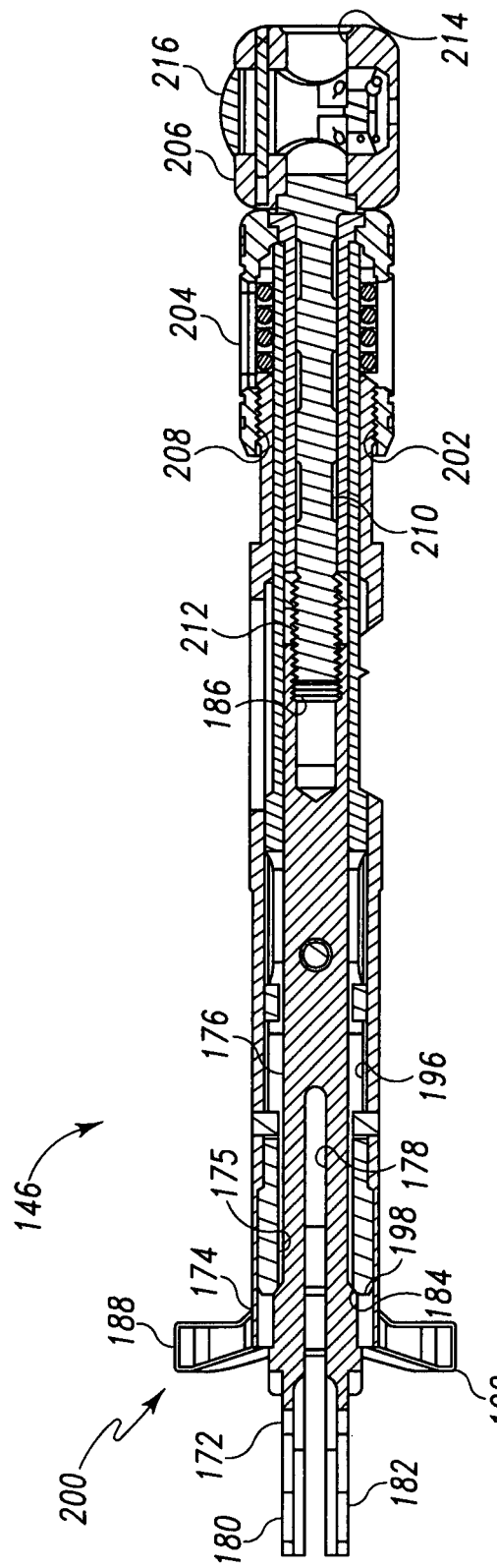
FIG. 4 shows a cross-sectional view of the prosthesis insertion assembly of FIG. 3 with a gripper partially inserted into the housing of the prosthesis insertion assembly and coupled with a coupling member incorporating features of the invention.

Next, the threaded portion 212 of the shaft 210 is engaged with the threads of the threaded blind bore 186 (see, e.g., FIG. 4). In the embodiment of FIG. 4, the coupling member 206 is rotationally coupled with the outer prosthesis insertion assembly housing 174 through the depth control member 204. In alternative embodiments, the coupling member may be separately provided. In such embodiments, the shaft of the coupling member is inserted into the inner channel 196 to allow coupling of the coupling member and the threaded blind bore 186.

Once the gripper 172 is coupled with the coupling member 206 within the housing 174 and with the disc prosthesis 100, rotation of the coupling member 206 causes the axial force with which the neck portion 184 is forced against the throat 198 to increase. When sufficient axial force is provided, the axial force is translated to a compressive force by the neck portion 184 being pressed against the throat 198. The gap 178 allows the arms 180 and 182 to move toward each other as indicated by the arrows 224 and 226 in FIG. 7 in response to the compressive force. As the arms 180 and 182 move toward each other, the diameter of the neck portion 184 narrows, allowing the stem 176 to move axially in the direction of the arrow 228, further into the inner channel 196.

The movement of the arms 180 and 182 is limited by the physical structure of the disc prosthesis 100. Thus, while some amount of movement may occur, once the arms 180 and 182 are firmly positioned against the disc prosthesis 100, continued rotation of the coupling member 206 primarily increases the gripping force which the arms 180 and 182 exert against the disc prosthesis 100, thereby providing a firm coupling. In embodiments wherein the disc prosthesis does not stop movement of the stem further into the inner bore, stops may be provided on the stem to restrict such axial movement after the desired gripping force is achieved.

Because the axial location of the prosthesis 100 is fixed with respect to the neck portion 184 at this point, and because the throat 198 provides a stop for the neck portion 184, the axial position of the prosthesis 100 with respect to the guides 188, 190, 192 and 194 is established by the depth established with the depth control member 204.

Figure 9:
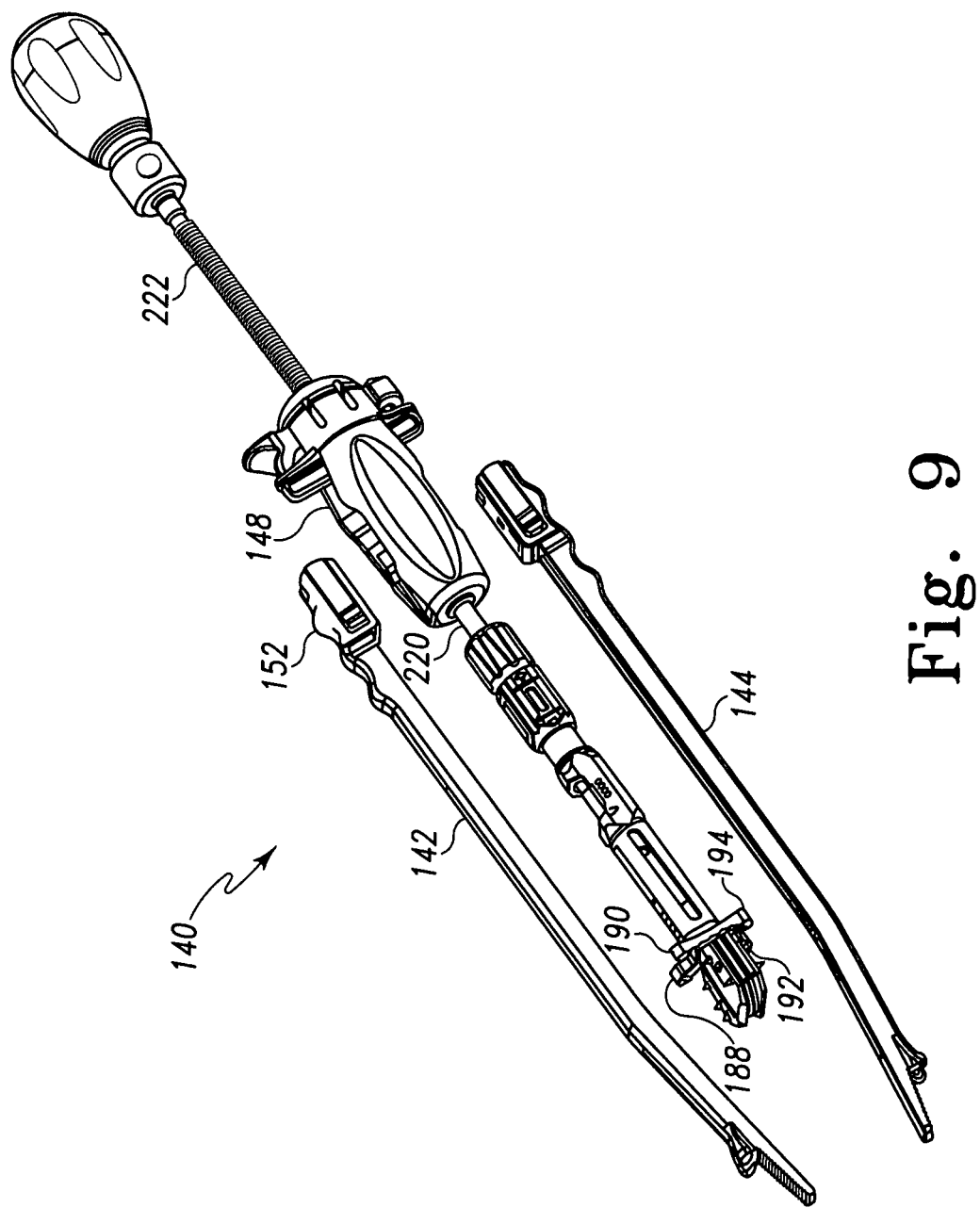
FIG. 9 shows an exploded perspective view of the system of FIG. 3 with the vertebra engaging members detached from the insertion assembly.

When the disc prosthesis 100 is firmly coupled with the prosthesis insertion assembly 146, the prosthesis insertion assembly 146 is coupled to the shaft 220 by insertion of the coupling portion 218 into the internal bore 214 resulting in the configuration shown in FIG. 9. Next, the vertebra engaging members 142 and 144 are connected to the base 148. As the vertebra engaging member 142 is connected, it is positioned within a space bordered by the guide members 188 and 190. Similarly, as the vertebra engaging member 144 is connected, it is positioned within a space bordered by the guide members 192 and 194 resulting in the configuration shown in FIG. 3.

Figure 10:
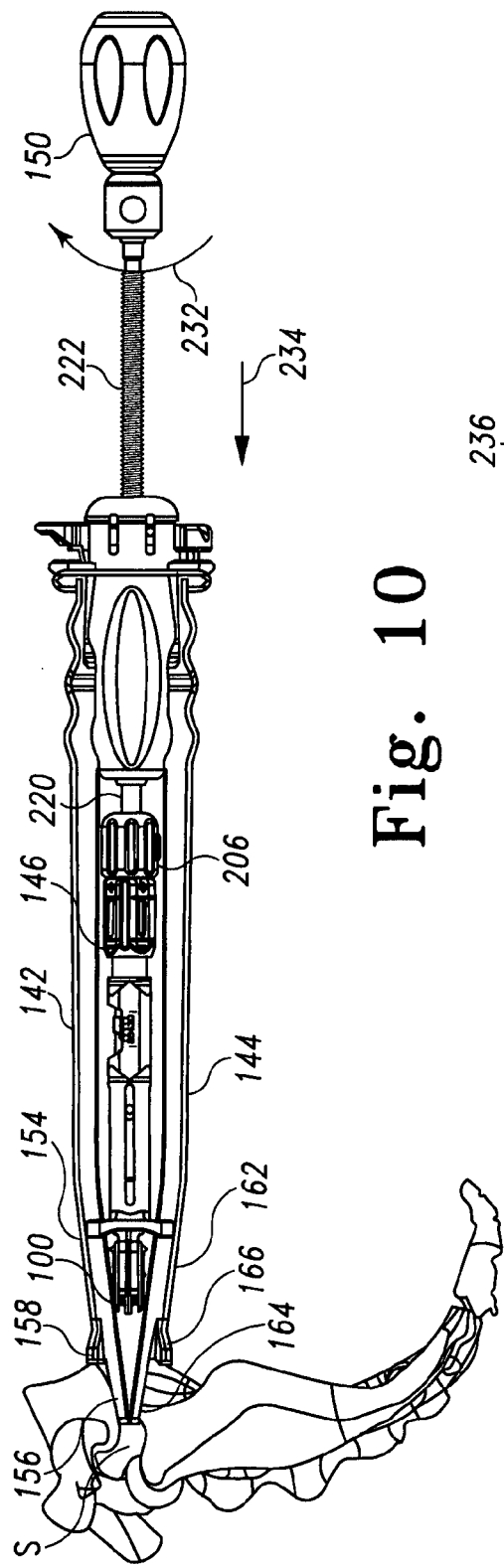
FIG. 10 shows a side plan view of the system of FIG. 3 with the fingers of the distraction instrument inserted into a space in which the disc prosthesis is to be implanted.

Referring to FIG. 10, once a space (S) has been prepared for receipt of the disc prosthesis 100 using any acceptable procedure, the fingers 156 and 164 are inserted into the space (S). Insertion of the fingers 156 and 164 into the prepared space (S) continues until the vertebra engaging members 158 and 166 contact the vertebras located adjacent to the prepared space (S) as shown in FIG. 10. Next, the knob 150 is rotated in the direction of the arrow 232 while the vertebral engaging members 158 and 166 are pressed against the vertebras adjacent to the prepared space. Because the threaded portion 222 of the shaft 220 is threadingly engaged with the base 148, rotation of the knob 150 causes the shaft 220 to move forwardly in the direction of the arrow 234 as well as rotate in the direction of the arrow 232.

The coupling portion 218 of the shaft 220 is free to rotate within the internal bore 214. Accordingly, as the shaft 220 rotates, the coupling member 206 does not rotate. The axial movement of the shaft 220, however, forces the prosthesis insertion assembly 146 to move forwardly in the direction of the arrow 234. As the prosthesis insertion assembly 146 moves, alignment with the vertebra engaging members 142 and 144 is maintained by the guides 188, 190, 192 and 194.

Figure 11:
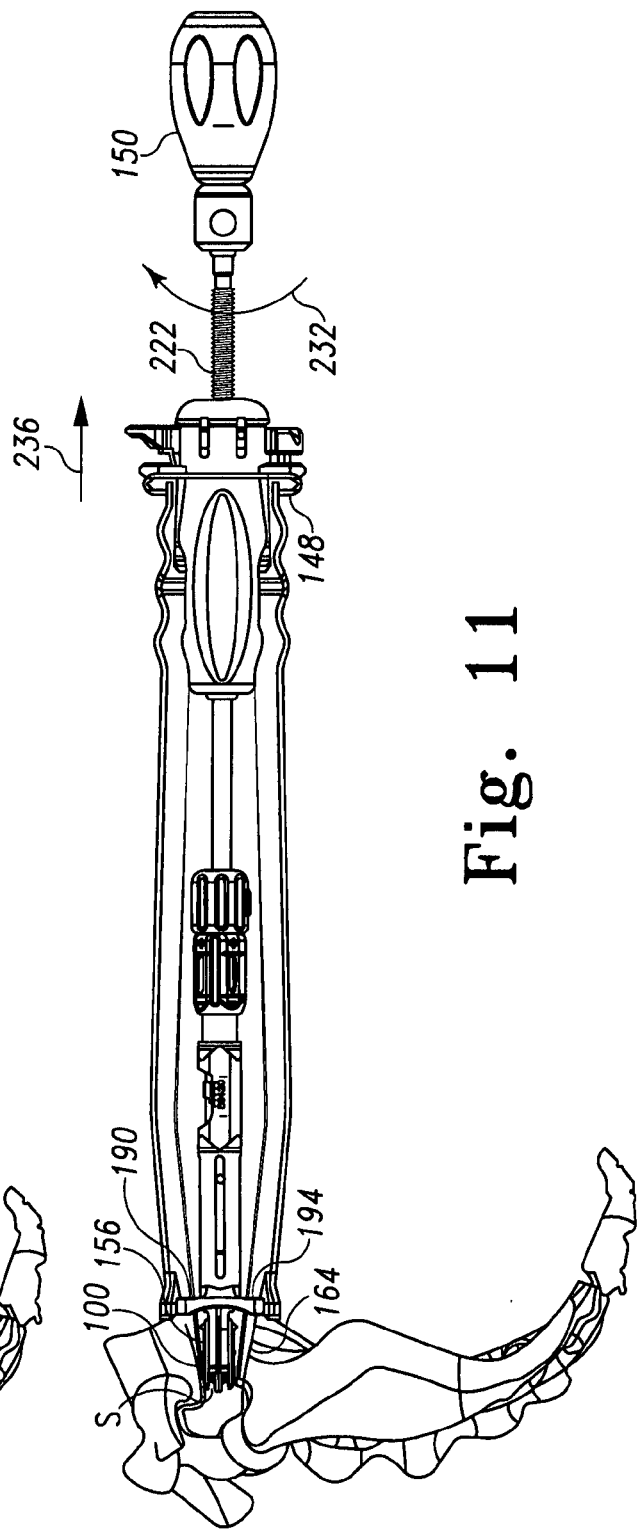
FIG. 11 shows a side plan view of the system of FIG. 3 with the disc prosthesis used to force the fingers of the distraction instrument into a distracted configuration in accordance with principles of the invention.

The axially forward movement of the prosthesis insertion assembly 146 forces the disc prosthesis 100 against the distal end portions 154 and 162 of the vertebra engaging members 142 and 144. This forces the fingers 156 and 164 against the vertebra adjacent to the prepared space (S), causing the vertebra to be forced apart and allowing the disc prosthesis 100 to move into the prepared space (S) as shown in FIG. 11.

As the disc prosthesis 100 moves into the space (S), the guide members 188, 190, 192 and 194 come into contact with the vertebrae adjacent to the space (s). Accordingly, further forward movement of the prosthesis insertion assembly 146 is restricted. Thus, as the knob 150 continues to be rotated in the direction of the arrow 232, the threaded portion 222 of the shaft 220 forces the base 148 to move in the direction of the arrow 236, thereby pulling the fingers 156 and 164 out of the space (S) while the disc prosthesis 100 remains in the space (S) as shown in FIG. 12.

Once the fingers 156 and 164 are clear of the space (S), the natural forces applied to the spinal column by the soft tissue attached to the spinal column will press the vertebrae adjacent to the space (S) against the disc prosthesis 100. Thus, the teeth 114 are imbedded into the adjacent vertebrae, fixing the disc prosthesis 100 in place. If desired, the prosthesis insertion assembly 146 may be decoupled from the disc prosthesis 100 simply by forcing the distraction instrument 140 away from the spine to overcome the friction lock.

Alternatively, the prosthesis insertion assembly 146 may be detached from the rest of the distraction instrument 140 as shown in FIG. 13 by depression of the release mechanism 216, which allows the shaft 220 to be removed from the internal bore 214. Next, the coupling member 206 is rotated in the direction indicated by the arrow 238. Such rotation of the coupling member 206 causes the neck portion 184 of the gripper 172 to be forced away from the throat 198 of the inner sleeve 175. Thus, the resilient nature of the gripper 172 forces the arms 180 and 182 in a direction away from the disc prosthesis 100.

The rotation of the coupling member 206 reduces the coupling force between the gripper 172 and the disc prosthesis 100. Accordingly, the gripper 172 may be decoupled from the disc prosthesis 100 by pulling on the coupling member 206.

Figure 5:
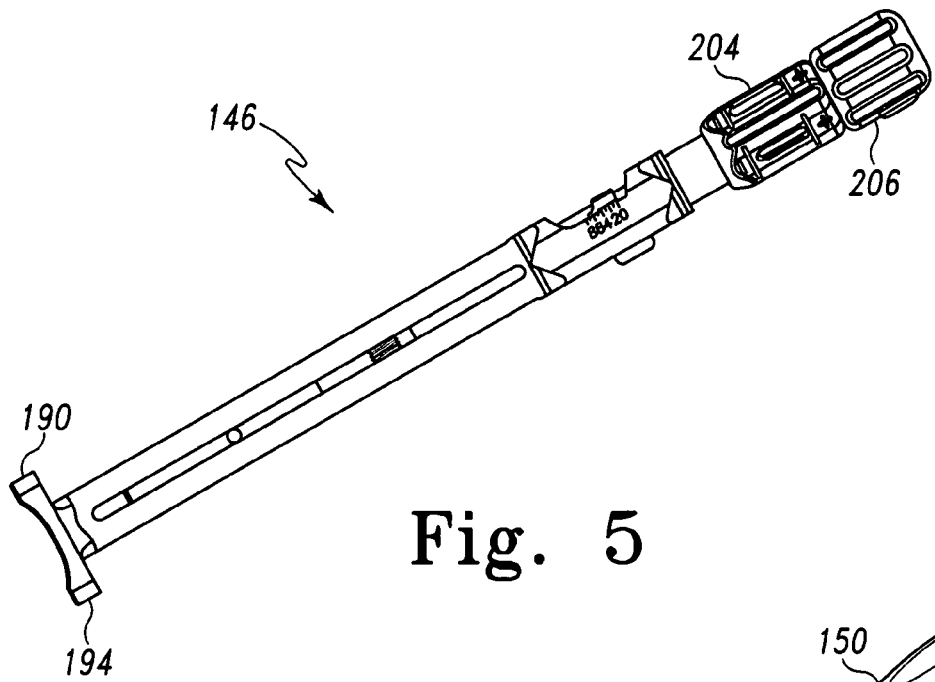
FIG. 5 shows a side plan view of the prosthesis insertion assembly of FIG. 3.
Figure 14:
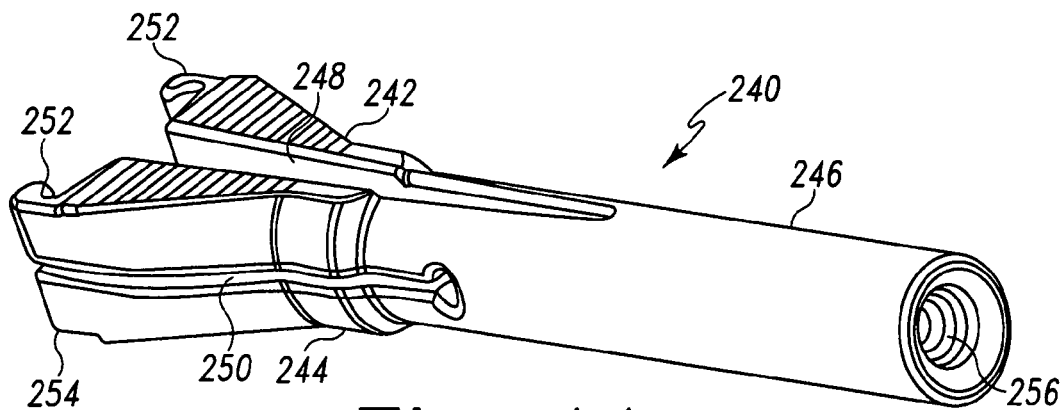
FIG. 14 shows an alternate embodiment of a gripper that may be used with the prosthesis insertion assembly of FIG. 5 in accordance with principles of the invention.

FIG. 14 shows an alternative gripper 240 which may be used with the prosthesis insertion assembly 146 of FIG. 5. The gripper 240 includes a coupling portion 242, a neck portion 244 and a stem 246 in an unstressed condition. The coupling portion 242 includes a slit 248 and a slit 250 which extend through the coupling portion 242 and the neck portion 244 into the stem 246. The slits 248 and 250 define two opposing pairs of arms 252 and 254 in the coupling portion 242 (only one arm of arm pair 254 is shown in FIG. 14). The neck portion 244 tapers from a larger diameter at the coupling portion 242 to a smaller diameter at the stem 246. The stem 246 includes a threaded inner bore 256 which is configured to be engaged with the threaded portion 212 of the coupling member 206.

Figure 15:
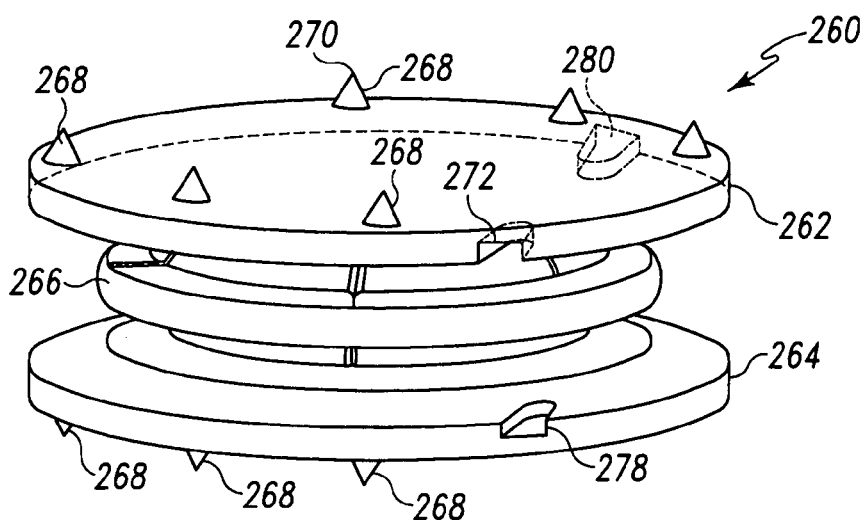
FIG. 15 shows an alternate embodiment of a disc prosthesis that may be used with the gripper of FIG. 14 in accordance with principles of the invention.

The coupling portion 242 of the gripper 240 is configured to mate with an artificial disc such as the artificial disc 260 shown in FIG. 15. The artificial disc 260 includes two endplates 262 and 264 which are separated by a core 266. Each of the two endplates 262 and 264 include a number of engagement members 268. In the embodiment of FIG. 15, the engagement members 268 are generally in the shape of a cone, with the apex 270 of the engagement members 268 spaced apart from the respective endplate 262 or 264. In alternative embodiments, the engagement members may be pyramidal, conical, or another shape. Preferably, the portions of the engagement members farthest away from the endplates, such as the apex of the engagement members 268, are relatively sharp.

Figure 16:
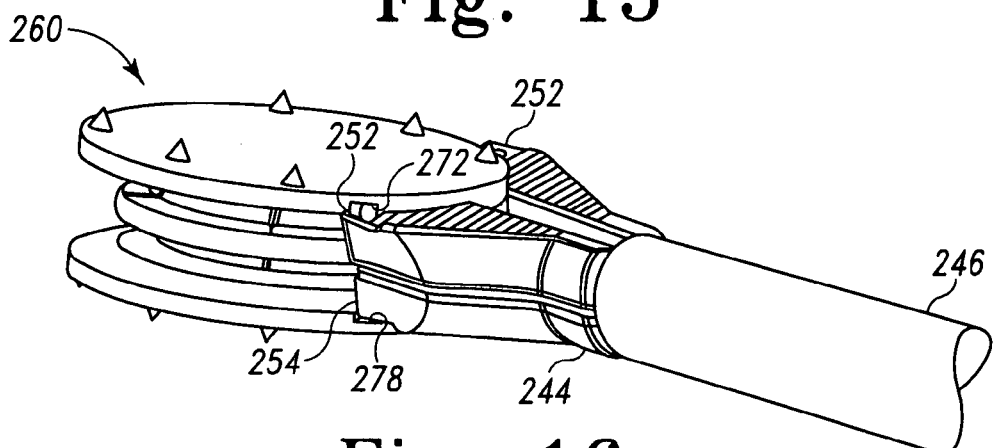
FIG. 16 shows the disc prosthesis of FIG. 15 coupled with the gripper of FIG. 14.

The endplates 262 and 264 further include four notches including notches 272 and 278 and two notches including the notch 280 and another notch not shown) that are symmetrical and spaced apart from the notches 272 and 278 to form two notch pairs. By way of example, the notch 280 which is shown in FIG. 16 in shadow form, is the symmetrical to and spaced apart notch for the notch 272. Thus, the notch 272 and the notch 280 are a notch pair.

The four notches, 272, 278, 280, and the notch not shown, are sized and shaped to snugly mate with the arms in the arm pairs 252 and 254. Moreover, the distance between each of the notches in the notch pairs is substantially the same as the distance between the opposing arms of the arm pairs 254 and 256 when the arm pairs 252 and 254 are in an unstressed condition. The configuration of the notches including shape and location, may be modified to optimize the control over the implant based upon the approach being used. For example, some implants may be configured to be used in an anterior approach whereas other may be configured for use in posterior or other approaches.

The gripper 240 is used in much the same manner as the gripper 172 described above. One difference, however, is that the configuration of the gripper 240 and the artificial disc 260 allows for a tighter coupling. Specifically, as depicted in FIG. 16, the arm pairs 252 and 254 engage the notches, 272, 278, 280, and the notch not shown, in a positive engagement as the individual arms are positioned within the notches, 272, 278, 280, and the notch not shown. Accordingly, when the neck portion 244 is pulled against the throat 198 by rotation of the coupling member 206 as described above, the axial force is translated to a compressive force whereby the arm pairs 252 and 254 engage the notches, 272, 278, 280, and the notch not shown more tightly and a very tight coupling is achieved between the gripper 240 and the artificial disc 260. Thus, the potential for unintentional decoupling is reduced.

Figure 17:
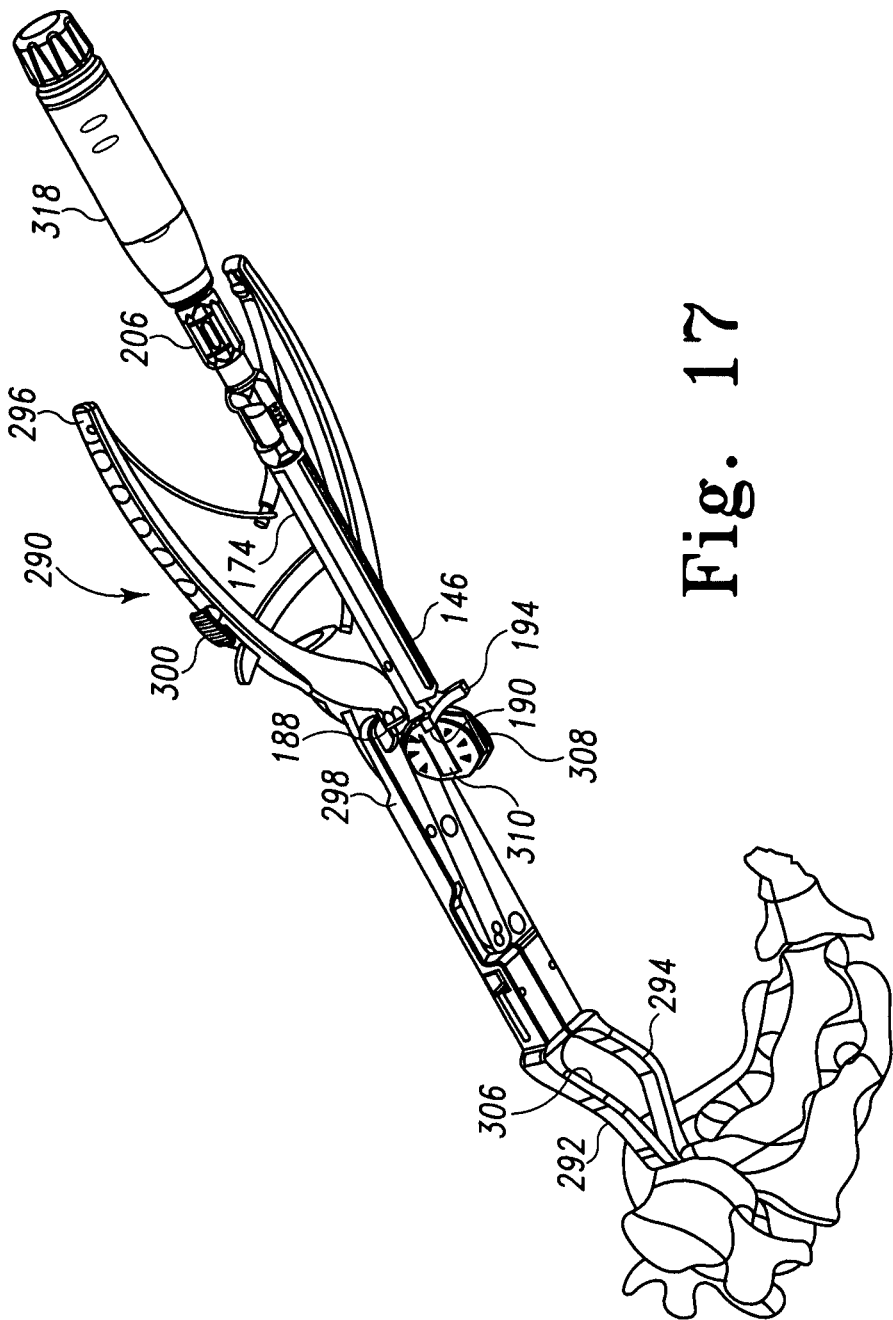
FIG. 17 shows a perspective view of an alternate implantation system incorporating the prosthesis insertion assembly of FIG. 5 and with the fingers of a distraction instrument inserted into a space in which the disc prosthesis is to be implanted.
Figure 18:
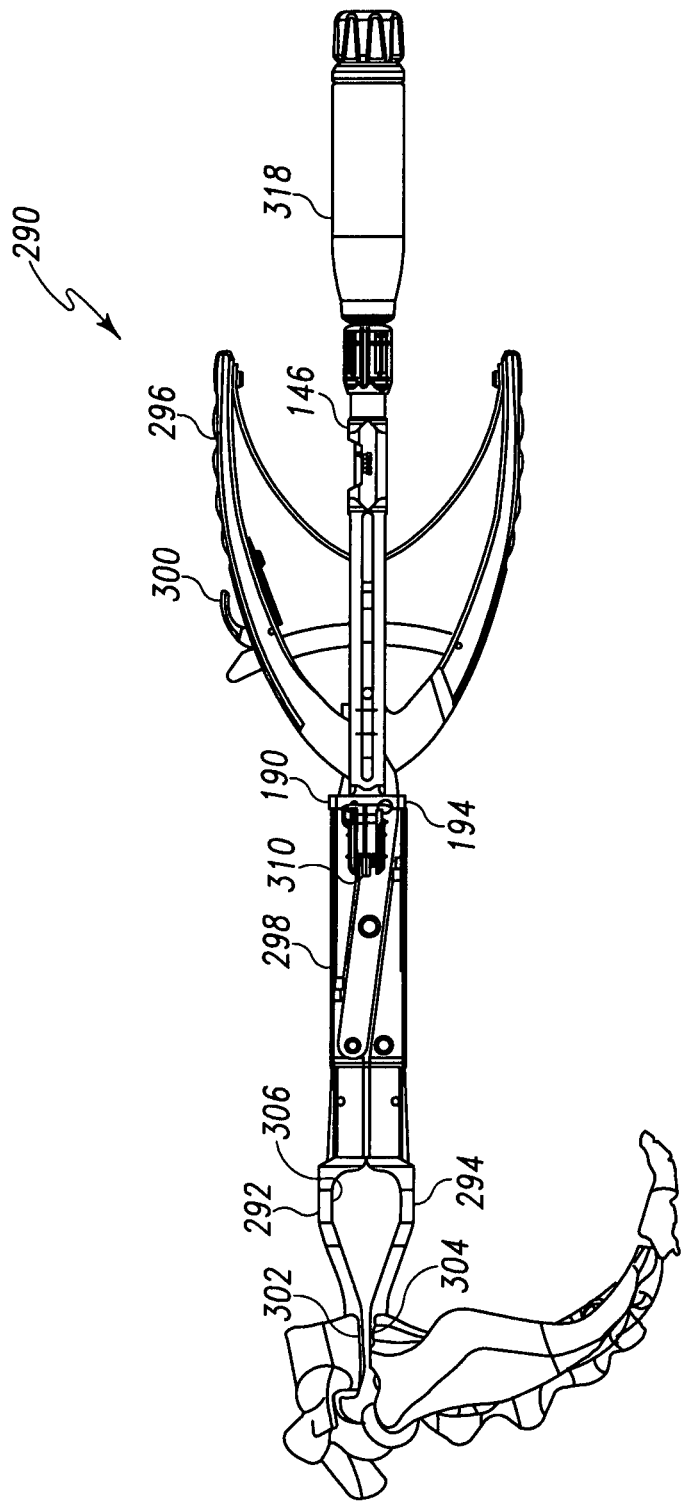
FIG. 18 shows a side plan view of the system of FIG. 17.

The prosthesis insertion assembly 146 may also be used with other distraction instruments such as the distraction instrument 290 shown in the system of FIGS. 17 and 18. The distraction instrument 290 includes a first vertebra engaging member 292 and a second vertebra engaging member 294. A handle 296 is provided on the instrument 290 along with a pivot assembly 298. A ratchet assembly 300 is located on the handle 296.

Fingers 302 and 304 extend from the vertebra engaging members 292 and 294, respectively. The upper vertebra engaging member 292 and the lower vertebra engaging member 294 are configured such that the finger 302 and the finger 304 converge from an insertion opening 306 defined by the upper vertebra engaging member 292 and the lower vertebra engaging member 294.

In the system of FIG. 17, a gripper 308 is coupled with a disc prosthesis 310 in the manner described above. An extension handle 318 is configured similarly to the coupling member 206 except that the extension handle 318 is longer than the coupling member 206. Thus, in a manner similar to the coupling member 206, the extension handle 318 is coupled to the disc prosthesis 310.

Operation of the system of FIG. 17 proceeds in a manner similar to the procedure described above with respect to the distraction instrument 140. One difference is that as shown in FIG. 17, the insertion assembly 146 need not be coupled with the distraction instrument 290 prior to the insertion of the fingers 302 and 304 into the space prepared for the disc prosthesis 310. Thus, after positioning the fingers 302 and 304 into the space prepared for the disc prosthesis 310, the extension handle 318 is used to manipulate the gripper 308 into position within the insertion opening 306.

When the gripper 308 is positioned within the insertion opening 306, the guide members 188 and 190 engage the upper vertebra engaging member 292 and the guide members 192 and 194 engage the lower vertebra engaging member 294. Thus, the disc prosthesis 310 is placed into the desired alignment. Either before or after the guide members 188, 190, 192 and 194 engage the upper vertebra engaging member 292 and the lower vertebra engaging member 294, the handle 296 is compressed, causing the upper vertebra engaging member 292 and the lower vertebra engaging member 294 to separate, thereby distracting the vertebra adjacent to the prepared space. As the handle 296 is compressed, the ratchet assembly 300 maintains the handle 296 in a compressed condition.

Figure 19:
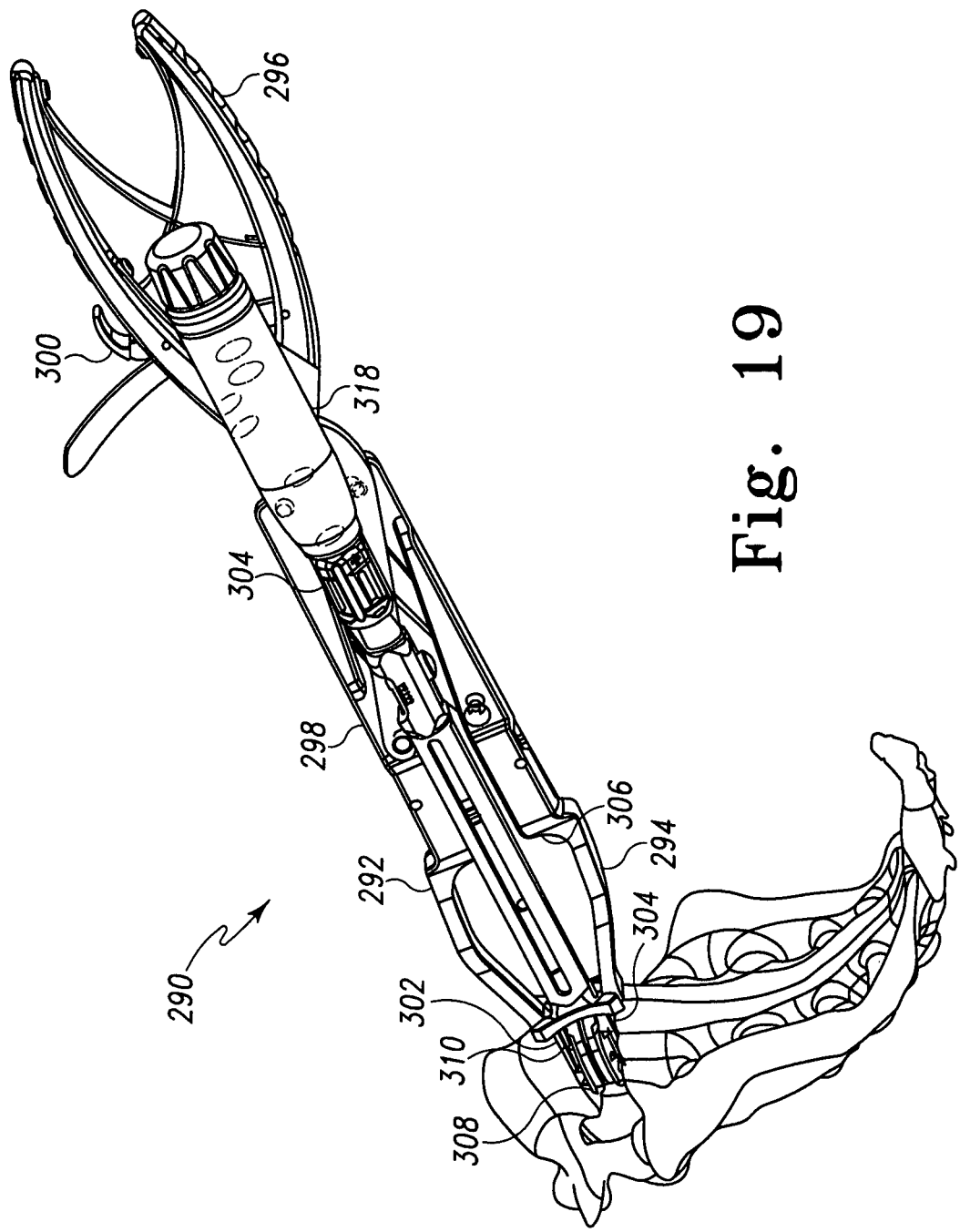
FIG. 19 shows a perspective view of the system of FIG. 17 after an extension handle has been used to position the disc prosthesis within the prepared space using guide members on the prosthesis insertion assembly to align the disc prosthesis in accordance with principles of the invention.

The disc prosthesis 310 is then positioned in the prepared space by guiding the gripper 308 toward the space with the guide members 188, 190, 192 and 194 engaging the upper vertebra engaging member 292 and the lower vertebra engaging member 294 until the guide members 188, 190, 192 and 194 contact the vertebra adjacent to the prepared space as shown in FIG. 19. In this condition, the disc prosthesis 310 is positioned within the spine at the depth set using the depth control member 304.

Figure 20:
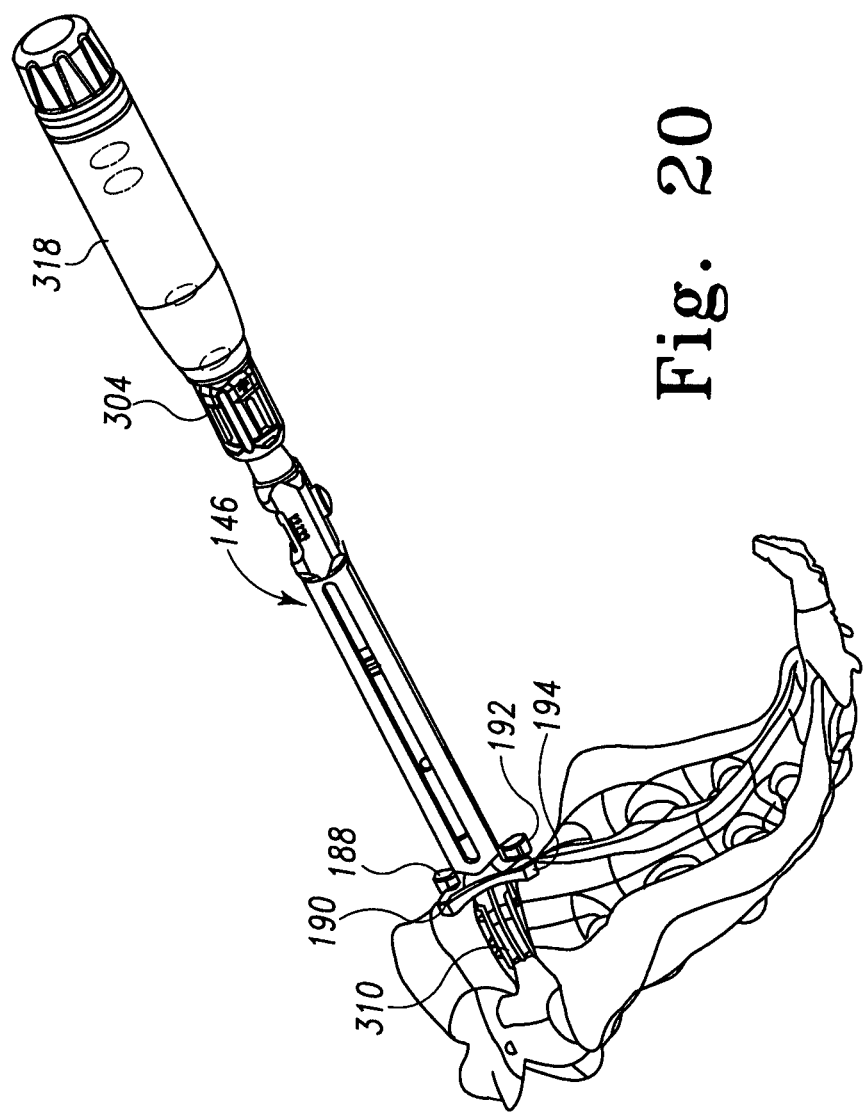
FIG. 20 shows a perspective view of the system of FIG. 17 after the distraction instrument has been removed, leaving the disc prosthesis in the prepared space.

Next, the distraction instrument 290 is removed by releasing the ratchet assembly 300. This allows the compressive force exerted on the spine by the surrounding soft tissue to force the vertebras adjacent to the space with the disc prosthesis 310 toward each other. This in turn forces the fingers 302 and 304 toward each other as the adjacent vertebras are pressed onto the teeth on the endplates of the disc prosthesis 310 resulting in the configuration of FIG. 20. Removal of the distraction instrument 290, the prosthesis insertion assembly 146 and the gripper 308 may then be accomplished in like manner to the previously set forth description.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

We claim:

1. A system for use in implanting a spinal prosthesis comprising:
    an insertion assembly housing with a channel extending from a distal end portion to a proximal end portion;
    a gripper having a prosthesis coupling portion configured to couple with a spinal prosthesis, and an end portion extending axially within the channel; and
    a coupler member having a gripper coupling portion rotatably positioned within the channel and configured to couple with the end portion of the gripper within the channel, wherein:

the end portion and the gripper coupling portion threadingly couple the gripper and the coupler member.

2. The system of claim 1, further comprising:
a depth control member threadingly engaged with the insertion assembly housing and rotatably coupled with the coupler member.

3. The system of claim 2, wherein the prosthesis coupling portion is configured to couple with a disc prosthesis.

4. The system of claim 3, wherein the prosthesis coupling portion is configured to maintain an assembled modular disc prosthesis as a unit by applying a compressive force on the assembled modular disc prosthesis.

5. The system of claim 1, wherein:
the distal end portion defines a first diameter of the channel; and
the gripper further comprises a translation portion for translating axial force to compressive force and having a second diameter, the second diameter larger than the first diameter, such that when the gripper is biased along an axis into the channel the translation portion cooperates with the distal end portion at the first diameter of the channel to force the prosthesis coupling portion toward the axis.

6. The system of claim 5, wherein:
the gripper comprises a stem having a third diameter, the third diameter smaller than the first diameter; and
the translation portion is located between the stem and the prosthesis coupling portion.

7. The system of claim 1, wherein the gripper coupling portion is at a first end portion of the coupler member and the coupler member further comprises an axial force receiving portion at a second end portion of the coupler member, the system further comprising:
a shaft including a threaded portion and an axial force transfer portion configured to transfer axial force to the axial force receiving portion;
a base threadingly engaged with the threaded portion of the shaft;
a first vertebra engaging member attached to the base and extending along the insertion assembly housing; and
a second vertebra engaging member attached to the base and extending along the insertion assembly housing.

8. The system of claim 7, wherein the first vertebra engaging member and the second vertebra engaging member define an insertion opening, the insertion opening sized to receive the prosthesis coupling portion.

9. The system of claim 8, the gripper further comprising:
at least one first guide member configured to maintain the gripper aligned with the first vertebra engaging member when the prosthesis coupling portion is positioned within the insertion opening; and
at least one second guide member configured to maintain the gripper aligned with the second vertebra engaging member when the prosthesis coupling portion is positioned within the insertion opening.

10. A method of positioning an implant, comprising:
identifying a vertebral implant;
coupling a gripper member with the vertebral implant;
rotating a coupler member within a housing to generate a first axial force on the gripper member;
translating the first axial force to a compressive force on the vertebral implant using the gripper member;
positioning the coupled vertebral implant;
decoupling the gripper member from the vertebral implant after the vertebral implant has been positioned; and
retracting two distraction arms by applying a second axial force to the housing prior to decoupling the gripper member.

11. The method of claim 10, wherein decoupling comprises:
pulling the gripper member away from the vertebral implant while the compressive force is translated onto the vertebral implant.

12. The method of claim 10, further comprising:
threadingly coupling the gripper with the coupler member; and
pulling at least a portion of the gripper into the housing using the coupler member.

13. The method of claim 12, further comprising:
determining an implantation depth for the vertebral implant; and
setting a depth control member on the housing based upon the determined implantation depth.

14. The method of claim 13, wherein setting a depth control member comprises:
axially positioning the depth control member along the axis of the housing.

15. The method of claim 10, further comprising:
engaging the gripper with an insertion assembly;
coupling the insertion assembly with a distraction instrument; and
separating the two distraction arms by pushing the gripper and the insertion assembly between the two distraction arms.

16. The method of claim 10, further comprising:
removing the compressive force from the vertebral implant prior to decoupling the gripper member from the vertebral implant.

17. A system for use in implanting a spinal implant comprising:
an insertion assembly housing having an axis;
a gripper with a spinal implant coupling portion configured to couple with a spinal implant, and a threaded portion; and
a coupling member configured to threadingly couple with the threaded portion of the gripper and to apply force to the gripper along the axis of the insertion assembly housing by rotation of the coupling member within the insertion assembly housing thereby forcing the spinal implant coupling portion toward the axis, wherein:
the coupling member is constrained against axial movement with respect to the insertion assembly housing;
the system further comprises a depth control member; and
the coupling member is axially constrained by the depth control member.

18. The system of claim 17, wherein:
the insertion assembly housing further comprises an opening extending from a first end portion of the insertion assembly housing to a second end portion of the insertion assembly housing;
the gripper comprises a longitudinally extending stem sized to fit within the opening at the first end portion;
the threaded portion of the gripper is located within a bore in the longitudinally extending stem; and
the coupling member comprises a shaft configured to fit within the opening at the second end portion and the threaded portion of the coupling member is on the shaft.

19. The system of claim 18, wherein
the gripper includes a tapered throat portion located between the longitudinally extending stem and the spinal implant coupling portion; and the insertion assembly housing further includes a neck located at the first end portion, a diameter of the neck less than a diameter of the throat whereby the gripper is constrained against axial movement with respect to the insertion assembly housing.

* * * * *